(12) United States Patent
Ellson et al.

(10) Patent No.: US 11,155,670 B2
(45) Date of Patent: Oct. 26, 2021

(54) AMORPHOUS THERMOSET THIOURETHANE POLYMERS, METHOD OF SYNTHESIS THEREOF AND USE IN BIO-ELECTRONIC DEVICES

(71) Applicant: Board of Regents, The University of Texas System, Austin, TX (US)

(72) Inventors: Gregory T. Ellson, Austin, TX (US); Walter Voit, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 152 days.

(21) Appl. No.: 16/316,876

(22) PCT Filed: Jul. 31, 2017

(86) PCT No.: PCT/US2017/044686
§ 371 (c)(1),
(2) Date: Jan. 10, 2019

(87) PCT Pub. No.: WO2018/038869
PCT Pub. Date: Mar. 1, 2018

(65) Prior Publication Data
US 2019/0300641 A1  Oct. 3, 2019

Related U.S. Application Data (60) Provisional application No. 62/378,976, filed on Aug. 24, 2016.

(51) Int. Cl.
| | | |
|---|---|---|
| C08G 18/73 | (2006.01) | |
| C08G 18/38 | (2006.01) | |
| A61L 31/02 | (2006.01) | |
| A61L 31/06 | (2006.01) | |
| A61L 31/08 | (2006.01) | |
| A61L 31/12 | (2006.01) | |
| C08G 18/75 | (2006.01) | |
| C08G 18/72 | (2006.01) | |
| C08G 18/20 | (2006.01) | |
| C08G 18/79 | (2006.01) | |
| A61N 1/05 | (2006.01) | |
| A61B 5/24 | (2021.01) | |

(52) U.S. Cl.
CPC ........ *C08G 18/3876* (2013.01); *A61L 31/022* (2013.01); *A61L 31/06* (2013.01); *A61L 31/088* (2013.01); *A61L 31/129* (2013.01); *C08G 18/2063* (2013.01); *C08G 18/725* (2013.01); *C08G 18/73* (2013.01); *C08G 18/755* (2013.01); *C08G 18/792* (2013.01); *A61B 5/24* (2021.01); *A61L 2420/02* (2013.01); *A61N 1/0551* (2013.01); *C08G 2280/00* (2013.01)

(58) Field of Classification Search
CPC .............. C08G 18/3876; C08G 18/725; C08G 18/2063; C08G 18/792; C08G 18/73; C08G 18/755; C08G 2280/00
See application file for complete search history.

(56) References Cited

U.S. PATENT DOCUMENTS

| | | | |
|---|---|---|---|
| 2003/0125410 A1* | 7/2003 | Keita ..................... | C08G 18/10 523/106 |
| 2004/0026658 A1* | 2/2004 | Yoshimura ......... | C08G 18/3876 252/183.11 |
| 2006/0111520 A1* | 5/2006 | Byers ................. | C08G 18/3876 525/452 |
| 2009/0143545 A1* | 6/2009 | Guerret .................. | G02B 1/041 525/92 C |
| 2014/0010858 A1 | 1/2014 | Stankus et al. | |
| 2014/0023866 A1 | 1/2014 | Rukavina et al. | |

FOREIGN PATENT DOCUMENTS

| | | |
|---|---|---|
| EP | 0065026 A1 | 11/1982 |
| WO | 2007149804 A2 | 12/2007 |
| WO | 2016126703 A1 | 8/2016 |
| WO | 2018038869 A1 | 3/2018 |

OTHER PUBLICATIONS

Campo, E.A.; Selection of Polymeric Materials: How to Select Design Properties from Different Standards, 2008, p. 103-140.*
Stille; "Step-Growth Polymerization"; Journal of Chemical Education; vol. 58(11); http://pubs.acs.org/doi/abs/10.1021/ed058p862; Nov. 1981; pp. 862-866.
Goodman; "Current and Future Uses of Gold in Electronics"; Gold Bulletin; https://link.springer.com/content/pdf/10.1007%2FB03214833.pdf; Feb. 4, 2002; pp. 21-26.
"Proven Capa and Tolonate synergy for high solids polyurethane coatings"; Perstorp Winning Formulas; eNewsletter; Issue Mar. 2009; http://cmpresinas.com.mx/abrirdoc.php?file=Sinergia%20para%20Recubrimientos%20para%20PU%20de%20Altos%20S%F3lidos.pdf; 2009; 2 pgs.

* cited by examiner

*Primary Examiner* — Robert S Jones, Jr.

(57) ABSTRACT

An amorphous thermoset thiourethane polymer, comprising a sequential chain of a first type of monomer covalently bonded to a second type of monomer via thiourethane linkages, wherein the first type of monomer includes two or more thiol functional groups and the second type of monomer includes two or more isocyanate functional groups. Methods of synthesizing the polymer, bio-electronic devices comprising the polymer and methods of manufacturing such devices are disclosed.

31 Claims, 10 Drawing Sheets

FIG. 1A

FIG 1B
IDI

FIG 1C
HDI

EDDT

FIG. 1E

HDI-T

AMORPHOUS THERMOSET THIOURETHANE POLYMERS, METHOD OF SYNTHESIS THEREOF AND USE IN BIO-ELECTRONIC DEVICES

CROSS-REFERENCE TO RELATED APPLICATION

This application is the National Stage of, and therefore claims the benefit of, International Application No. PCT/US2017/044686 filed on Jul. 31, 2017, entitled "AMORPHOUS THERMOSET THIOURETHANE POLYMERS, METHOD OF SYNTHESIS THEREOF AND USE IN BIO-ELECTRONIC DEVICES," which was published in English under International Publication Number WO 2018/038869 on Mar. 1, 2018; which claims benefit to U.S. Provisional Application No. 62/378,976 filed on Aug. 24, 2016, entitled "AMORPHOUS THERMOSET THIOURETHANE POLYMERS, METHOD OF SYNTHESIS THEREOF AND USE IN BIO-ELECTRONIC DEVICES". The above application is commonly assigned with this National Stage application and is incorporated herein by reference in its entirety.

TECHNICAL FIELD

This application is directed, in general, to amorphous thermoset thiourethane polymers and more specifically, tough softenable forms of such polymers, methods of synthesis, and, use of such polymers in bio-electronic devices.

BACKGROUND

The use of chronically implanted bio-electronic devices can sometimes be hampered by a failure over time in the device's ability to record and/or stimulate neural signals. Various reasons suggested for this failure include neuroinflammatory responses, device failure, or chronic damage to surrounding tissue. Some forms of device failure have been attributed to large, orders of magnitude, higher elastic modulus of some device substrates as compared to living tissue. However, device substrates having a modulus comparable to tissue can be difficult to implant without damaging the device or restoring to more invasive surgical procedures to ensure successful implantation. The use of mechanically adaptive substrates, whose modulus can decrease such that the substrate is rigid ex vivo and soft in vivo appears to be a promising approach. Shape memory thermoset polymers can undergo a glass transition, resulting in a large decrease in modulus. Substrates composed of certain shape memory acrylic networks may have large cure stresses which, in turn can make it difficult to fabricate electronics components (e.g., metal traces) thereon. Substrates composed of certain thiol-ene/acrylate shape memory polymers have low cure stresses but such polymers may only soften in vivo to a modulus 20-100 MPa which is still orders of magnitude higher than some tissues such as brain (5 kPa). Thus, there is a continuing need to develop shape memory polymer substrates with softening and mechanical performance for use in bio-electronic devices.

SUMMARY

The present disclosure provides in one embodiment, an amorphous thermoset thiourethane polymer comprising a sequential chain of a first type of monomer covalently bonded to a second type of monomer via thiourethane linkages, wherein the first type of monomer includes two or more thiol functional groups and the second type of monomer includes two or more isocyanate functional groups.

In some such embodiments, the polymer can have a glass transition Tg in a range from about 0° C. to 80° C. In some such embodiments, the polymer can have a rubbery modulus in a range from about 0.01 MPa to 100 MPa.

In any such embodiments, the first type of monomer can include one or more of: Trimethylolpropane tris(3-mercaptopropionate); Trimethylolpropane tris(2-mercaptoacetate); Pentaerythritol tetrakis(2-mercaptoacetate); Pentaerythritol tetrakis(3-mercaptopropionate); 2,2'-(Ethylenedioxy)diethanethiol; 1,3-Propanedithiol; 1,2-Ethanedithiol; 1,4-butanedithiol; 1,5-pentanedithiol; 1,6-hexanedithiol; 1,9-nonanedithiol; xylene dithiol; Thiobis(benzenethiol); 1,4-Butanediol bis(thioglycolate); 1,4-bis(3-mercaptobutylyloxy)butane; Tris[2-(3-mercaptopropionyloxy)ethyl]isocyanurate; 3,4-ethylenedioxythiophene; 1,10-Decanedithiol; Tricyclo[5.2.1.02,6]decanedithiol; Benzene-1,2-dithiol; and Trithiocyanuric acid.

In any such embodiments, the second type of monomer can include one or more of: hexamethylene diisocyanate; isophorone diisocyanate; diisocyanatobutane; diisocyanatooctane; 1,3,5-Tris(6-isocyanatohexyl)-1,3,5-triazinane-2,4,6-trione; phenylene diisocyanate; xylylene diisocyanate; tolyene diisocyanate; cyclohexylene diisocyanate; toluene iisocyanate; and methylenebis(phenyl isocyanate).

Some such embodiments can further include a third type of monomer having a single thiol functional group or a single isocyanate functional group. In some such embodiments, the third type of monomer having the single thiol functional group can include one or more of: 1-butanethiol; 1-hexanethiol; 1-heptanethiol; 1-octanethiol; 1-nonanethiol; 1-decanethiol; and 1-octadecanethiol. In some such embodiments, the third type of monomer having the single isocyanate functional group can include one or more of: propyl isocyanate; 1-pentyl isocyanate; hexyl isocyanate; octyl isocyanate; nonyl isocyanate; sec-butyl isocyanate; 2-ethylhexyl isocyanate; cyclopentyl isocyanate; and 1-isocyanato-3-methylbutane.

In some such embodiments, the first type of monomer can include a linear main chain monomer having the thiol-functionalized groups at ends of the chain and the second type of monomer can include a linear main chain monomer having the isocyanate functional groups at ends of the chain, and, a bulky non-crystallizable segment-containing monomer or a tri- or higher functionalized isocyanate monomer. In some such embodiments a total mole percentage the thiol functional groups of the first type of monomer equals about 100 mole percent of the linear main chain monomer having the thiol-functionalized groups, and, a total mole percentage of the isocyanate groups of the second type of monomer equals about 5 to 25 mole percent of the linear main chain monomer having the isocyanate functional groups, about 55 to 65 mole percent of the bulky non-crystallizable segment-containing monomer and about 20 to 40 mole percent the tri- or higher functionalized isocyanate monomer, wherein the total mole percentage of the isocyanate functional groups is substantially equal to the total mole percentage of the thiol functional groups of the first type of monomer. In some such embodiments, the linear main chain monomer having the thiol-functionalized groups can be 2,2'-(Ethylenedioxy)diethanethiol, the linear main chain monomer having the isocyanate functional groups can be hexamethylene diisocyanate, the bulky non-crystallizable segment-containing monomer can be isophorone diisocyanate, and the tri- or higher functionalized isocyanate monomer can be Tris(6-isocyanatohexyl)isocyanurate.

Another embodiment of the disclosure is a method of synthesizing any embodiments of the amorphous thermoset thiourethane polymers as disclosed herein. Synthesizing an amorphous thermoset thiourethane polymer can comprise forming a mixture that includes a first type of monomer and a second type of monomer, wherein the first type of monomer and the second type of monomer are mutually miscible liquids and adding to the mixture a non-nucleophilic base catalyst having a pKa greater than 7. An anionic step-growth polymerization reaction is thereby initiated to form a sequential chain of the first type of monomer covalently bonded to the second type of monomer via thiourethane linkages, wherein the first type of monomer includes two or more thiol functional groups and the second type of monomer includes two or more isocyanate functional groups.

In some such embodiments the mixture is solvent free. In some such embodiments, adding of the non-nucleophillic base catalyst to the mixture can include: adding a photolatent base to the mixture and irradiating the mixture with UV or visible light to decompose the photolatent base into the non-nucleophillic base, wherein the non-nucleophillic base includes a tertiary amine. In some such embodiments, adding of the non-nucleophillic base catalyst to the mixture can include: adding a tertiary amine containing catalyst that is soluble in the mixture and heating the mixture to a temperature of about 100° C. for at least about 1 hour. In any such embodiments, a total mole percentage of the isocyanate groups in the mixture can be substantially equal to a total mole percentage of the thiol functional groups of the first type of monomer in the mixture.

Another embodiment is bio-electronic device that comprises a substrate composed of any of the embodiments of the amorphous thermoset thiourethane polymers as disclosed herein. The amorphous thermoset thiourethane polymer includes a sequential chain of a first type of monomer covalently bonded to a second type of monomer via thiourethane linkages, wherein the first type of monomer includes two or more thiol functional groups and the second type of monomer includes two or more isocyanate functional groups. In some such embodiments the device can be further patterned with gold adhered to the amorphous thermoset thiourethane polymer.

Still another embodiment of the disclosure is a method of manufacturing a bio-electronic device that comprises any embodiments of the amorphous thermoset thiourethane polymers disclosed herein. The method comprises providing first and second glass substrates, the substrates spaced apart by a gap, wherein a major surface of the first glass substrates facing the gap is coated with a layer of gold and further comprises forming any embodiments of the amorphous thermoset thiourethane polymers disclosed herein on the gold layer. Forming the polymer can include placing a mixture in the gap such that the mixture contacts the layer of gold, the mixture including a first type of monomer and a second type of monomer, wherein the first type of monomer and the second type of monomer are mutually miscible liquids. Forming the polymer can also include adding to the mixture a non-nucleophillic base catalyst having a pKa greater than 7 to thereby initiate an anionic step-growth polymerization reaction to form a sequential chain of the first type of monomer covalently bonded to the second type of monomer via thiourethane linkages, wherein the first type of monomer includes two or more thiol functional groups and the second type of monomer includes two or more isocyanate functional groups.

Any such embodiments can further include separating the glass substrates from each other, wherein one side of the amorphous thermoset thiourethane polymer adheres to a major surface of the second glass substrate and the gold layer is adhered to an opposite side of the amorphous thermoset thiourethane polymer. Any such embodiments can further include photolithographically patterning the gold layer to form lines of the bio-electronic device. Any such embodiments can further include separating the amorphous thermoset thiourethane polymer from the major surface of the second glass substrate.

BRIEF DESCRIPTION OF DRAWINGS

For a more complete understanding of the present disclosure, reference is now made to the following detailed description taken in conjunction with the accompanying FIGUREs. Reference is now made to the following descriptions taken in conjunction with the accompanying drawings, in which:

FIG. 1 presents schematic representations of: A) a thiol-isocyanate click reaction to synthesize amorphous thermoset thiourethane polymers of the disclosure; B) an example cyclic monomer having two isocyanate functional groups C) an example linear monomer having two isocyanate functional groups D) an example cyclic monomer having three isocyanate functional groups E) an example linear monomer having two thiol functional groups and F) the synthesis of the photo-catalyst QAS-BP.

DETAILED DESCRIPTION

Embodiments of the amorphous thermoset thiourethane polymers are disclosed to soften by three orders of magnitude in simulated in vivo conditions while retaining their mechanical integrity and toughness. The modulus of embodiments of the polymers under simulated in vivo conditions more closely match the modulus of biological tissue and to our knowledge these the polymers have higher mechanical toughness than other types of shape memory polymers. We believe that the combination of softening ability under simulated in vivo conditions and mechanical toughness of the disclosed polymers will improve the longevity and chronic performance of bio-electronic devices by reducing inflammation, scarring and/or mechanical failure in vivo.

It may be surprising that such thiourethane polymers are promising candidates to serve as substrates for bio-electronic devices. For instance, isocyanates are known toxins, and one type of the monomer reactants used to synthesize these thiourethane polymers includes isocyanate functional groups. Leaching of such unreacted monomers, e.g., due to incomplete curing of the thiourethane polymer, raises the possibly that an implanted electronic device that includes a thiourethane polymer substrate, could have cytotoxic effects. However, thiourethane polymer reaction kinetics in the presence of a base catalyst are substantially faster than, e.g., polyurethane reaction kinetics. Consequently, the polymerization reaction to form the disclosed thiourethane polymers, is thought to proceed to completion with little to no byproducts in ambient conditions. However, such fast reaction kinetics may make it challenging to process due to the rapid reaction rates.

The amorphous thermoset thiourethane polymers disclosed herein were discovered to have increased moisture uptake and higher glass transition temperatures, e.g., as compared to thiol-ene shape memory polymers. These properties are thought to be due to the rigid, polar thiourethane bonds formed from the thiol-isocyanate coupling. The extensive hydrogen bonding generated by the thiourethane linkage also results in more robust materials, similar to polyurethanes. To our knowledge the use of polythiourethanes as a tough softening material for in vivo application is previously unrecognized.

As illustrated below, the design of softening bio-electronic devices that include substrate embodiments of these thiourethane polymers benefited due to these materials having tunable thermomechanical properties to enable softening following implantation into the body. These thiourethane polymers are also thermally stable to ensure compatibility with photolithographic processes. These thiourethane polymers are also mechanically robust enough to survive implantation and chronic operation in vivo.

The ability of a polymer substrate to soften is highly dependent on the macromolecular structure of the substrate. The modulus beyond the glass transition temperature is a factor of both the crosslinking density and degree of crystallinity in the material. Amorphous polymers which exhibit no long-range order (crystallinity) offer desirable softening capability due to having the least amount of interaction between polymer chains above the glass transition temperature (Tg). Semi-crystalline polymers with low glass transition temperatures tend to have moduli in the range of 100s of MPa, while amorphous counterparts can soften to moduli well below 10 MPa, for example down to about 200 kPa.

The amorphous thermoset thiourethane polymers of the disclosure are designed to soften around an engineered Tg in which softening is not disrupted by a higher temperature melting transition that would result in semi-crystalline thermoset thiourethane polymers. As further disclosed herein, engineering the Tg benefits from the use of steric hindrance, or the ability of monomer side chains that are not part of the backbone or main chain non-crystallizable segments to disrupt crystalline structures that otherwise might form during polymerization.

One embodiment of the disclosure is an amorphous thermoset thiourethane polymer. The polymer comprises a sequential chain of a first type of monomer covalently bonded to a second type of monomer via thiourethane linkages. The first type of monomer includes two or more thiol functional groups and the second type of monomer includes two or more isocyanate functional groups. The first and second types of monomers are polymerized together in an anionic step-growth polymerization reaction that is catalyzed by a non-nucleophillic base having a pKa greater than 7 and/or by heat.

Embodiments of the amorphous thermoset thiourethane polymer have a glass transition Tg in a range from about 0° C. to 80° C. and a rubbery modulus, Er, in a range from about 0.01 MPa to 100 MPa.

Non-limiting examples of the first type of monomer having two or more thiol functional groups include: Trimethylolpropane tris(3-mercaptopropionate); Trimethylolpropane tris(2-mercaptoacetate); Pentaerythritol tetrakis(2-mercaptoacetate); Pentaerythritol tetrakis(3-mercaptopropionate); 2,2'-(Ethylenedioxy)diethanethiol; 1,3-Propanedithiol; 1,2-Ethanedithiol; 1,4-butanedithiol; 1,5-pentanedithiol; 1,6-hexanedithiol; 1,9-nonanedithiol; xylene dithiol; Thiobis(benzenethiol); 1,4-Butanediol bis(thioglycolate); 1,4-bis(3-mercaptobutylyloxy)butane; Tris [2-(3-mercaptopropionyloxy)ethyl]isocyanurate; 3,4-ethylenedioxythiophene; 1,10-Decanedithiol; Tricyclo[5.2.1.02, 6]decanedithiol; and Benzene-1,2-dithiol; Trithiocyanuric acid.

Non-limiting examples of the second type of monomer having two or more isocyanate functional groups include: Hexamethylene diisocyanate; isophorone diisocyanate; diisocyanatobutane; diisocyanatooctane; 1,3,5-Tris(6-isocyanatohexyl)-1,3,5-triazinane-2,4,6-trione; phenylene diisocyanate; xylylene diisocyanate; tolyene diisocyanate; cyclohexylene diisocyanate; and toluene diisocyanate; methylenebis(phenyl isocyanate).

In any embodiments a third type of monomer may be added where each of the third type of monomer has a single thiol functional group or a single isocyanate functional group. Such mono-functionalized monomers may be used to facilitate chain capping and branched networks in the thiourethane polymer and/or limit the molecular weight of the thiourethane polymer.

Non-limiting example embodiments of the third type of monomer having a single thiol functional group include: 1-butanethiol; 1-hexanethiol; 1-heptanethiol; 1-octanethiol; 1-nonanethiol; 1-decanethiol; and 1-octadecanethiol. Non-limiting example embodiments of the third type of monomer having a single isocyanate functional group include: propyl isocyanate; 1-pentyl isocyanate; hexyl isocyanate; octyl isocyanate; nonyl isocyanate; sec-butyl isocyanate; 2-ethylhexyl isocyanate; cyclopentyl isocyanate; and 1-isocyanato-3-methylbutane.

Another embodiment of the disclosure is a method of synthesizing the amorphous thermoset thiourethane polymers as disclosed herein. The method comprises forming a mixture that includes a first type of monomer and a second type of monomer, the monomers being mutually miscible liquids. The method also comprises adding to the mixture a non-nucleophillic base catalyst having a pKa greater than 7 to thereby initiate an anionic step-growth polymerization reaction to form a sequential chain of the first type of monomer covalently bonded to the second type of monomer via thiourethane linkages, wherein, the first type of monomer includes two or more thiol functional groups and the second type of monomer includes two or more isocyanate functional groups.

Embodiments of the polymerization reaction occur in a solvent free environment (e.g., about 1 wt percent solvent or less or about 0.1 wt percent or less in some embodiments). Embodiments of the polymerization reaction can be catalyzed by photolatent bases, compounds which upon irradiation with light (e.g., UV or visible light), can decompose into components which include a non-nucleophillic base such as a tertiary amine containing catalyst. Embodiments of the polymerization reaction can be catalyzed by liquid catalyst bases (e.g., tertiary amine containing catalyst soluble in the mixture). Embodiments of the polymerization reaction can additionally or alternatively be catalyzed by heat.

To further illustrate various features of the disclosure, the synthesis of non-limiting example amorphous thermoset thiourethane polymers and some of their properties are presented below.

FIG. 1 presents schematic representations of: A) a thiol-isocyanate click reaction to synthesize amorphous thermoset thiourethane polymers of the disclosure; B) an example cyclic monomer having two isocyanate functional groups C) an example linear monomer having two isocyanate functional groups D) an example cyclic monomer having three isocyanate functional groups E) a example linear monomer having two thiol functional groups and F) the synthesis of the photo-catalyst QAS-BP.

In some embodiments, to facilitate a complete reaction of monomers, the total amount of all of the isocyanate functionalized monomers can be adjusted such that a total mole percentage of the isocyanate groups substantially equals a total mole percentage of the thiol functional groups of the first type of monomer (e.g., within about ±10 percent and in some embodiments, within about ±1 percent).

The crystallinity and rubbery modulus of the thermoset thiourethane polymer produced in the polymerization reaction (FIG. 1A) can be engineered by adjusting the composition of the second type of monomers (e.g., the monomers shown in FIGS. 1B, 1C and 1D) so as to provide different proportions of these isocyanate functionalized monomers.

Figure 1A:
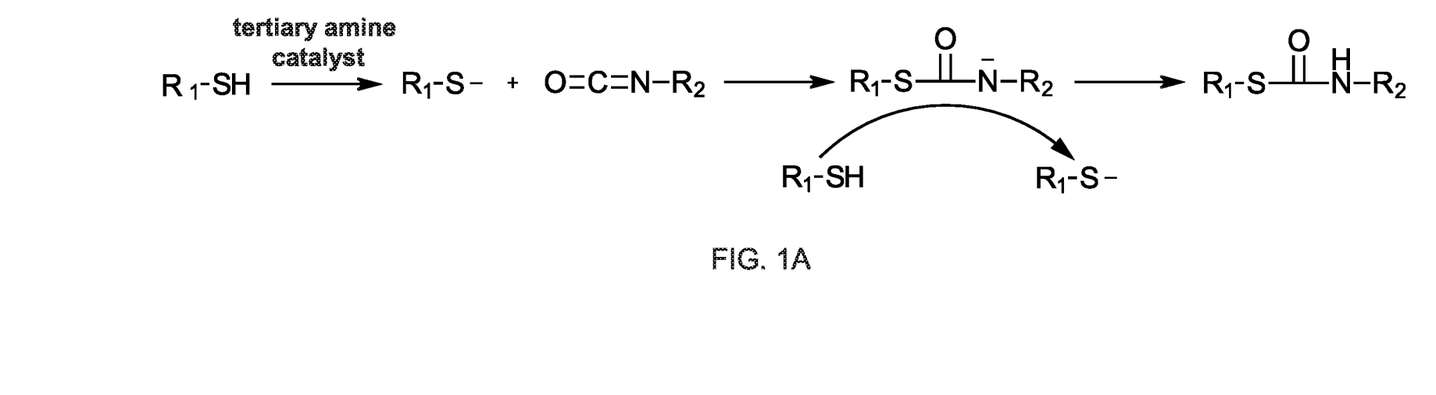
Figure 1B:
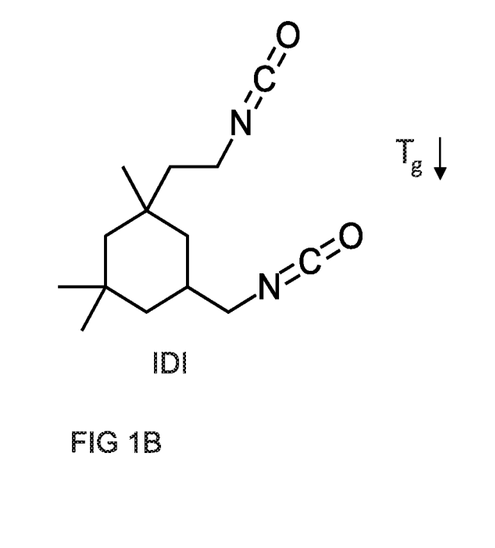
Figure 1C:
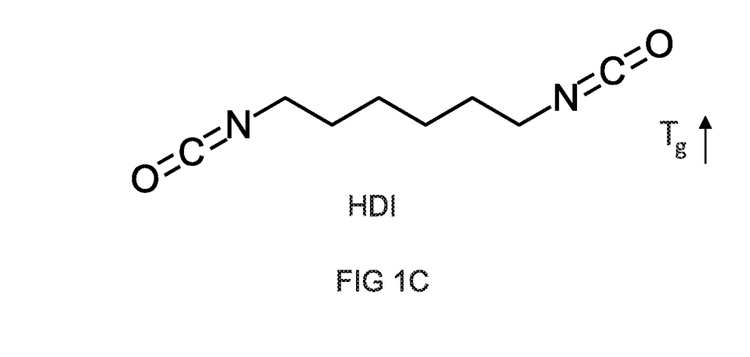
Figure 1D:
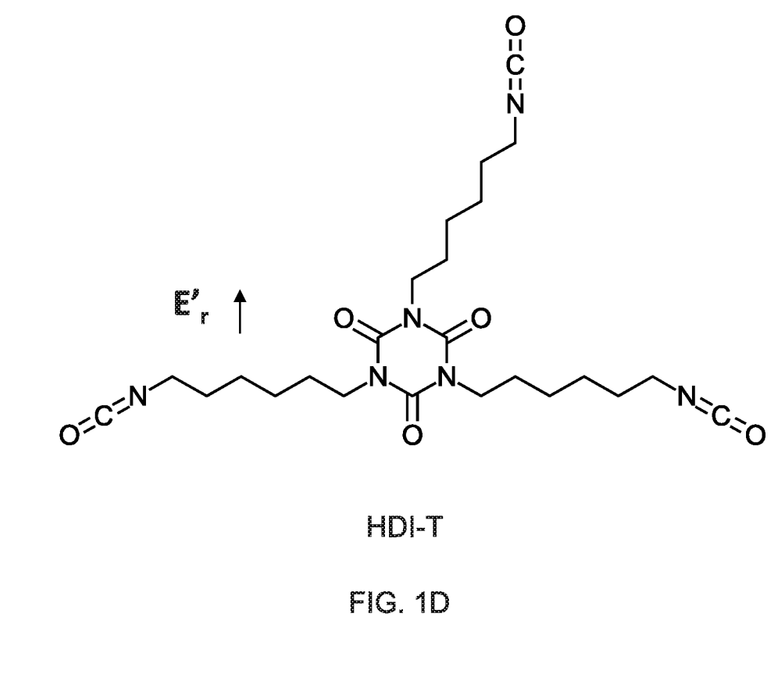

For instance, for some embodiments, such as indicated by the arrows in FIGS. 1B and 1C, increasing proportions of IDI decreases Tg while increasing proportions of HDI increases Tg of the resulting polymer. The isocyanate functionalized monomers can be selected so as to disrupt the crystallinity of the main polymer chain to produce embodiments of the amorphous thermoset thiourethane polymer. For example, the isocyanate-functionalized monomer isophorone diisocyanate (IDI) (FIG. 1B) has a bulky non-crystallizable segment, that when incorporated into the main chain in sufficient proportions, disrupts packing of the linear chains of the thiol-functionalized first type of monomer 2,2'-(ethylenedioxy)diethanethiol (EDDT) (FIG. 1E) and the linear chains of the second type of monomer Hexamethylene diisocyanate (HDI) (FIG. 1C). In limited proportions, for example, IDI can influence Tg and other material properties including the extent of crystallization, but not prevent the formation of crystals that limit softening.

For instance, small proportions (e.g., 25 mol % or less) of isocyanate functionalized monomers or thiol-functionalized monomers having bulk side chains may be selected so as to similarly disrupt the crystallinity of the thermoset thiourethane polymer. As an example, isobornyl acrylate side chains, or other bulky side chains can be incorporated into the first and or second types of monomers.

Based on the present disclosure, one skilled in the pertinent art would understand how combinations of such main chain and side chain crystallinity disrupting monomers could be incorporated into the first and second types of monomers to engineer amorphous thermoset thiourethane polymers having a target Tg range and does not have a high melt temperature melt and thus will still soften.

Figure 1E:
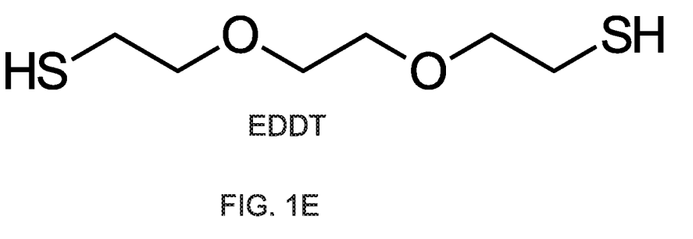

For instance illustrated by the arrow in FIG. 1E in some embodiments, increasing proportions of HDI-T can increase the rubbery modulus ($E_r$) of the resulting polymer. Tri- or higher functionalized isocyanate functionalized monomers, such as Tris(6-isocyanatohexyl)isocyanurate (HDT-T) (FIG. 1E), or similar tri- or higher thiol-functionalized monomers, can be selected in proportions to promote cross-linking between growing polymer main chains, resulting thermoset thiourethane polymers with an increased rubbery modulus.

To further illustrate these principles amorphous thermoset thiourethane polymer composed of these monomers were synthesized and some of their physical properties, cytotoxicity and manufacturability characteristics were assessed.

Figure 1F:
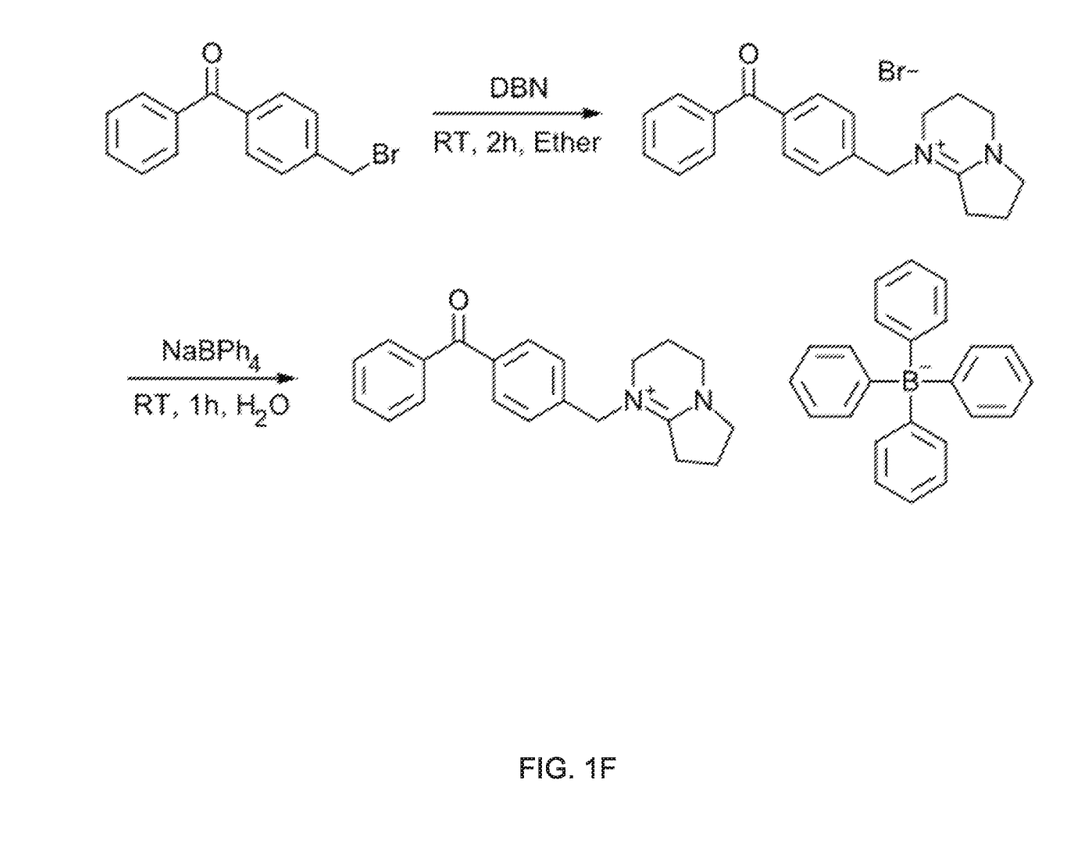

Amorphous Thermoset Thiourethane Polymers Synthesis:

Stoichiometric mixtures of 2,2'-(ethylenedioxy)diethanethiol (EDDT), hexamethylene diisocyanate (HDI), isophorone diisocyanate (IDI), and the trimer of hexamethylene diisocyanate (HDI-T) were mixed with the previously synthesized photo-catalyst, QAS-BP until homogenous. FIG. 1F presents a schematic representation of the synthesize of the photo-catalyst QAS-BP (5-(4'-(bromomethyl)benzophenone)-1,5-diazabicyclo[4.3.0]non-5-ene tetraphenylborate). The pre-polymer solution was injected between glass slides separated by 100 μm or 500 μm spacers. The resins were cured for 30 minutes under 365 nm irradiation in a UVP CL-1000L ultraviolet crosslinker (UVP, LLC, Upland Calif.) prior to undergoing a thermal post-cure at 100° C. for at least one hour.

The stiffness of the polymer substantially depends on its glass transition temperature and the crosslink density. The crosslink density was adjusted by selecting the amount of HDI-T added to the reaction mixture, as the three functional groups present on the molecule can act as a cross-linker between growing polymer chains. The glass transition of the substrate was tuned by adjusting the ratio of HDI and IDI. A polymer formed with more of the flexible HDI monomer would exhibit a lower glass transition than a polymer formed with more of the rigid IDI monomer. By using different proportions of HDI, IDI, and HDI-T with EDDT it was possible to independently control the degree of crosslinking and the glass transition temperature. The different polymer compositions were prepared by choosing a proportional amount of the cross-linking monomer, HDI-T (e.g., 20 or 40 mol % of the isocyanate functional groups), and adjusting the ratios of HDI and IDI (e.g., as mol % of the isocyanate functional groups) such that the glass transition temperature was tuned to different temperatures in a desired range. Table 1 presents the proportions of the monomers used to formulate example sample polymer compositions.

TABLE 1 amorphous thermoset thiourethane polymer compositions

| Composition | Functional Group Percentage | | | |
|---|---|---|---|---|
|  | EDDT | HDI | IDI | HDI-T |
| TU-40 | 100 | 5 | 55 | 40 |
| TU-20 | 100 | 20 | 60 | 20 |

Physical Properties:

Thermogravimetric analysis was performed on a Mettler Toledo TGA/DSC 1. Samples were cut into circular disks approximately 3 mm in diameter and 500 µm thick and placed in 70 µL alumina crucibles. The samples were heated from 25° C. to 700° C. at 10° C. min$^{-1}$ under nitrogen flow. The thermal degradation onset was determined using the Mettler Toledo STARe Thermal Analysis Suite. At least three samples were tested for each polymer composition.

Figure 2:
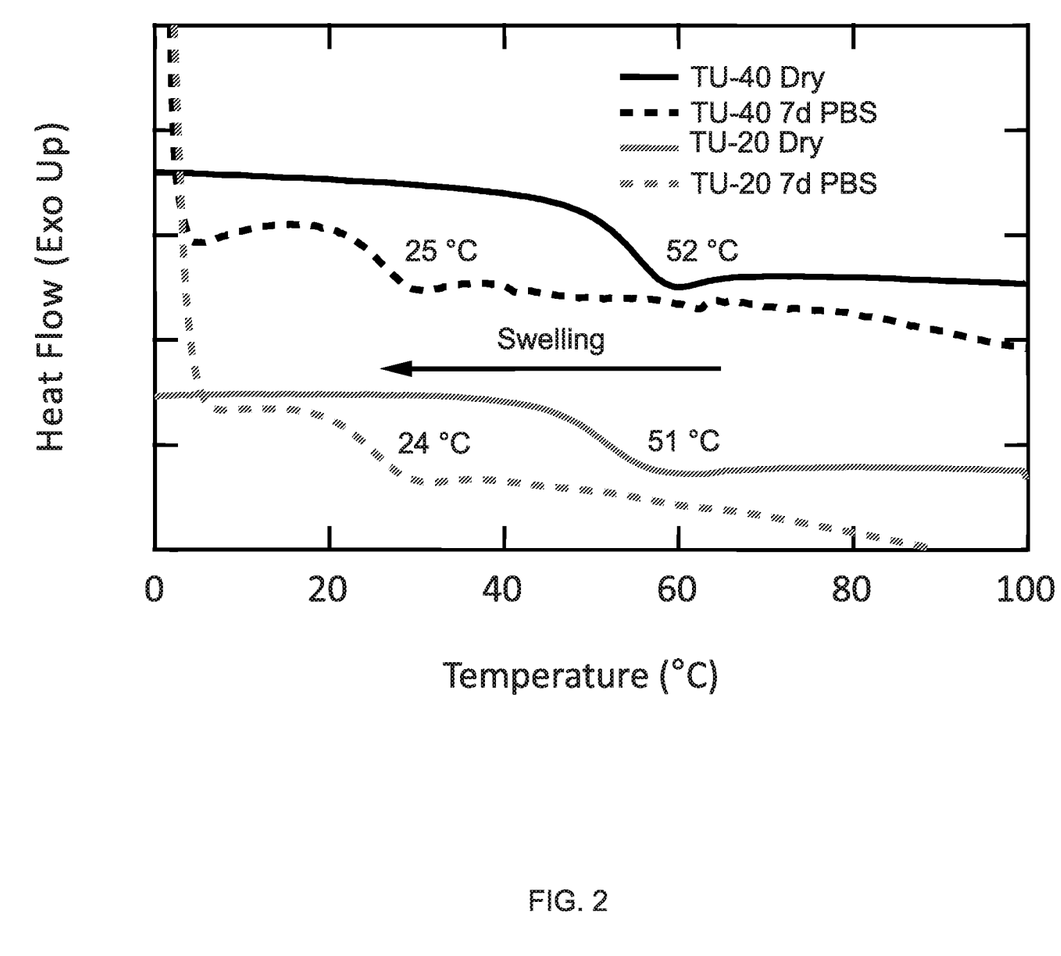
FIG. 2 presents example differential scanning calorimetry (DSC) heating ramps of sample embodiments of the amorphous thermoset thiourethane polymers as disclosed herein, the samples in a dry state or after 7 days exposure to phosphate buffered saline (PBS)

FIG. 2 presents example differential scanning calorimetry (DSC) heating ramps of sample embodiments of the amorphous thermoset thiourethane polymers as disclosed herein, the samples in a dry state or after 7 days exposure to phosphate buffered saline (PBS).

DSC was performed on a Mettler Toledo DSC1/700. Samples were cut into circular disks 3 mm in diameter and 500 µm thick and placed in 40 µL aluminum crucibles. Dry samples were inserted at 50° C. and cooled to −50° C. before undergoing three heating and cooling cycles between −50° C. and 150° C. The second and third cycles were used to determine polymer Tg. Wet samples were inserted at 25° C. and cooled to 0° C. before heating to 100° C. Only one cycle was performed as subsequent cycles would result in dehydration of the sample. All heating rates were 10° C. min$^{-1}$. Glass transition temperature was determined using the Mettler Toledo STARe Thermal Analysis Suite. At least three samples were tested for each polymer composition.

As shown in FIG. 2, the glass transition temperatures of the sample polymers and the shift in glass transition temperature in the presence of simulated physiological conditions was characterized by DSC. Both substrates have glass transition temperatures slightly above 50° C. when dry. We believe this will facilitate bio-electronic device substrates formed from such polymers having enough rigidly to e.g., undergo insertion into the body without damaging electronic components located on the substrate prior to polymer softening.

Samples were soaked in PBS solution at 37° C. to simulate exposure to physiological conditions. Following one week of immersion, both substrates were re-tested and displayed a 27° C. downward shift in glass transition temperature. This suggests that the substrates may undergo complete softening once implanted, as the final glass transition temperatures of substrates TU-40 and TU-20 are 12° C. and 13° C. below that of physiological temperatures, respectively.

Figure 3:
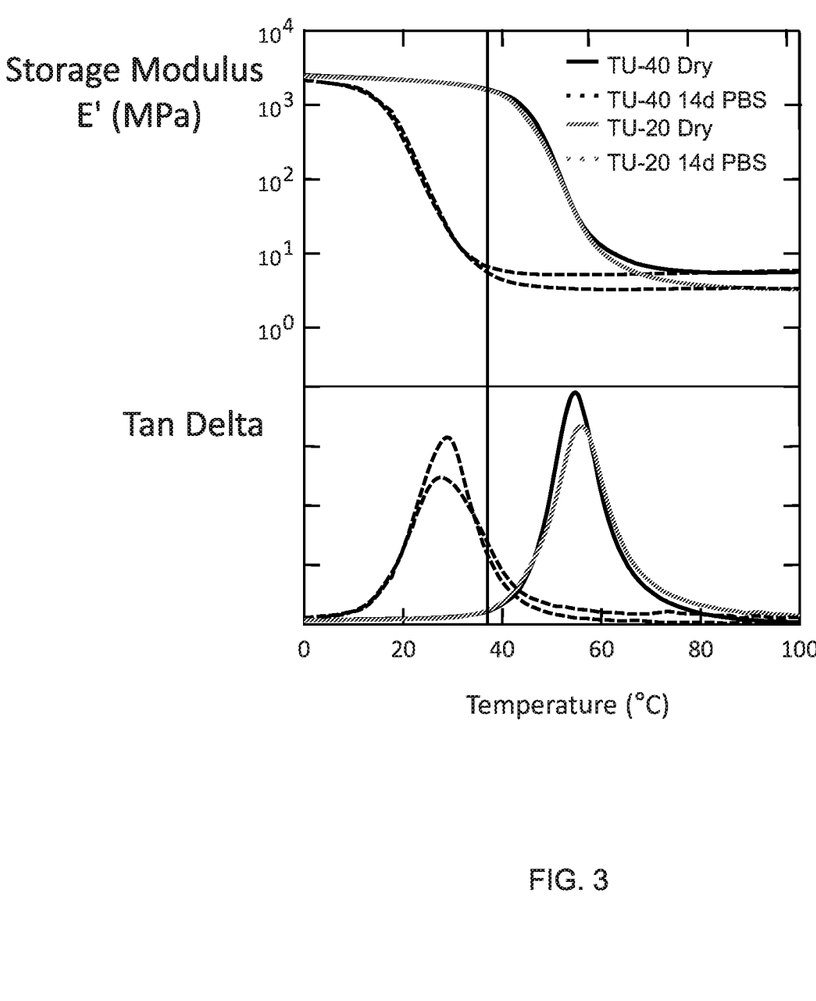
FIG. 3 presents example dynamic mechanical analysis (DMA) scans of sample embodiments of the amorphous thermoset thiourethane polymers as disclosed herein, the samples being in a dry state or after 14 days exposure to PBS.

FIG. 3 presents example dynamic mechanical analysis (DMA) scans of sample embodiments of the amorphous thermoset thiourethane polymers as disclosed herein, the samples being in a dry state or after 14 days exposure to PBS.

DMA was performed on a Mettler Toledo DMA/SDTA861e. Samples were cut into rectangular bars 30 mm long, 3 mm wide, and 500 µm thick. Samples were loaded into the large tension assembly and underwent a heating ramp from 0° C. to 100° C. at 2° C. min$^{-1}$. The samples were oscillated at 1 Hz with a force limit of 5 N and strain limit of 0.2% with a 300% offset. The glass transition by DMA was determined as the peak of tan δ. At least three samples were tested for each polymer composition.

Prior to insertion, both substrates had moduli of about 1800 MPa at 37° C. The glass transition onset was beyond 40° C., suggesting that water uptake occurred in order for the substrate to soften. Once through the glass transition the two substrates show behavior dependent on their crosslink density. The more highly cross-linked density TU-40 has a rubbery modulus of 5.7 MPa while the lower cross-linked density TU-20 has a modulus of 4.0 MPa. Following 14 days of immersion in PBS at 37° C. the glass transition shifts downward. The substrates are almost completely through the glass transition at 37° C., with TU-40 and TU-20 exhibiting moduli of 6.7 MPa and 5.6 MPa, respectively. This represents a three-order of magnitude decrease in modulus, due to water uptake.

Figure 4:
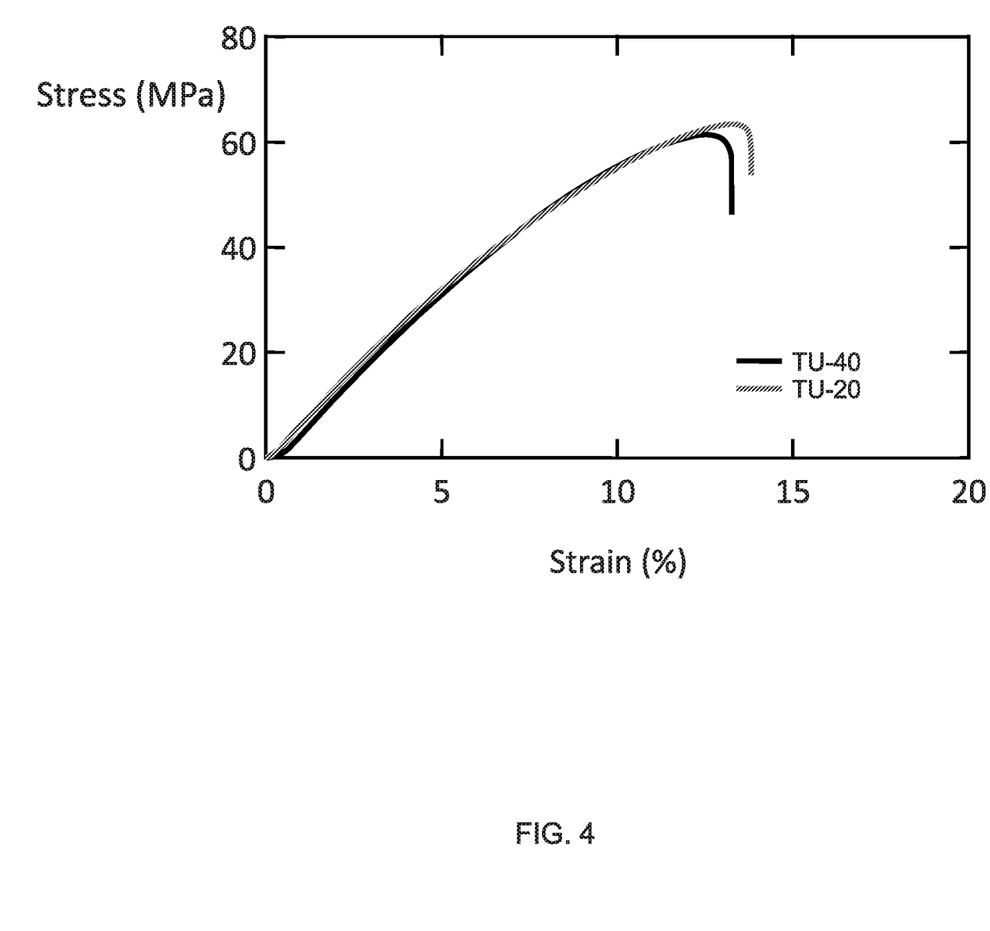
FIG. 4 presents example tensile test stress-strain curves of sample embodiments of the amorphous thermoset thiourethane polymers as disclosed herein, the samples in a dry state.
Figure 5:
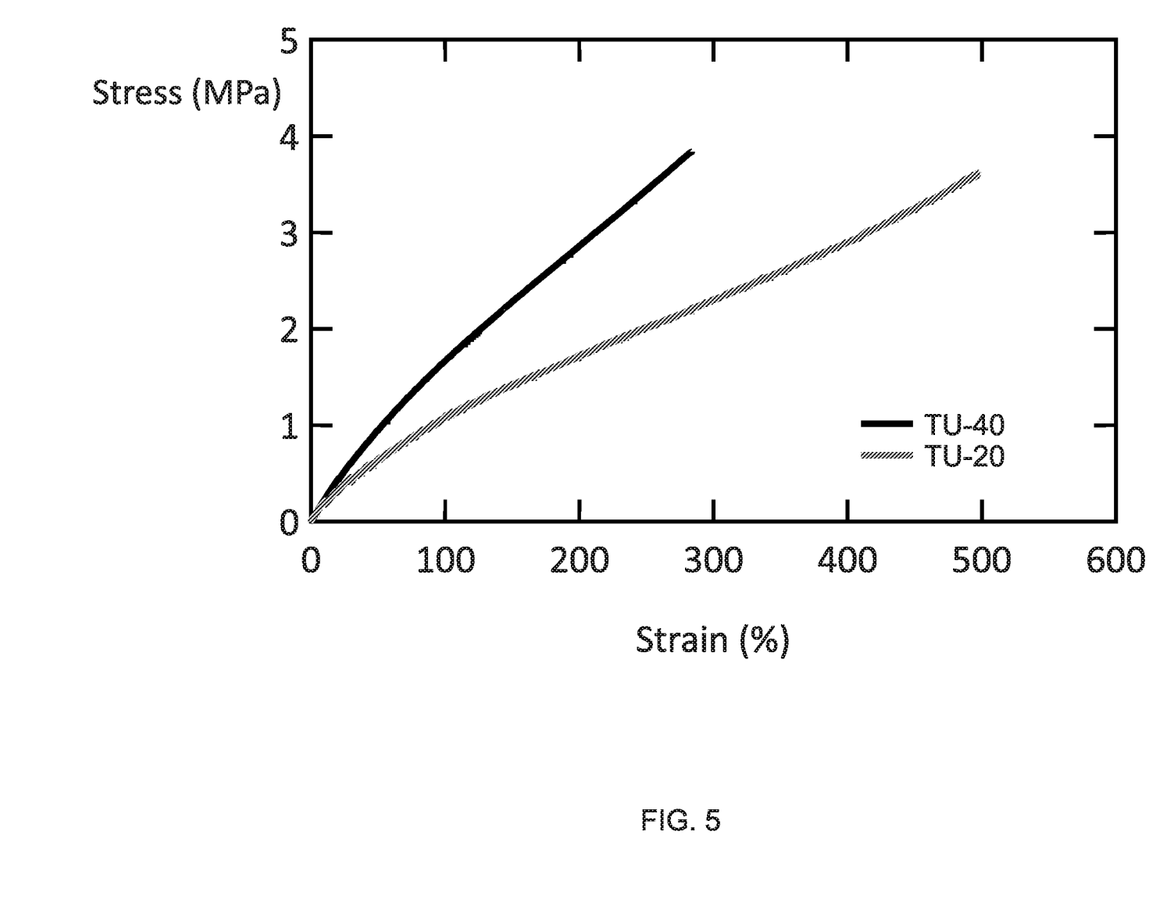
FIG. 5 presents example tensile test stress-strain curves of sample embodiments of the amorphous thermoset thiourethane polymers as disclosed herein, the samples in a wet state.

FIG. 4 presents example tensile test stress-strain curves of sample embodiments of the amorphous thermoset thiourethane polymers as disclosed herein, the samples in a dry state. FIG. 5 presents example tensile test stress-strain curves of sample embodiments of the amorphous thermoset thiourethane polymers as disclosed herein, the samples in a wet state. The tests were uniaxial quasi-static tension tests performed strain-to-failure on thin film substrate samples of the polymers TU-40 and TU-20.

As illustrated in FIG. 4, substrate samples of both TU-40 and TU-20 demonstrated similar tensile performance when dry, as the substrates have not gone through their glass transitions. The tensile performance changed substantially in the simulated physiological conditions as illustrated in FIG. 5. Both substrates exhibit characteristically rubbery behavior, failing at below 4 MPa but at strains of 280% and 500% for TU-40 and TU-20, respectively. We attributed the substantial difference in strain capacity to the different expected crosslink density of these substrates. For instance, embodiments of TU-20, with approximately half of the expected crosslink density of TU-40, have a nearly two times the strain capacity of TU-40.

The swelling and degradation behavior of the sample substrates was investigated by determining the water uptake and mass loss following drying while in simulated physiological conditions.

There was concern that embodiments of bio-electronic devices that include substrate composed of such amorphous thermoset thiourethane polymers could encounter device failure, e.g., due to excessive swelling due to water uptake resulting in damage or delamination of electronic components on the substrate. Limiting the amount swelling such that the substrate softens but occur to the extent of causing such device failure is an important balance that is achievable by engineering the composition and proportions of monomers used to form these polymers.

There was also concern that embodiments of bio-electronic devices that include substrate composed of such amorphous thermoset thiourethane polymers could slowly degrade in vivo with subsequent delamination of the electronic components from the degraded substrate. Such degradation can be mitigated by engineering the composition and proportions of monomers used to form these polymers.

Samples of TU-20 an TU-40 were cut into disks approximately 3 mm in diameter and 500 µm thick. The disks were individually massed and submerged in individual well plates with phosphate buffered saline solution. Samples were soaked at 37° C. for 1, 4, 7, 14, or 28 days prior to testing. On each of these days, 3 disks of each composition were removed and patted dry before being massed to determine the degree of swelling. The samples were then dried under vacuum at 125° C. for at least 12 hours before being massed once more to determine the degree of degradation.

Figure 6:
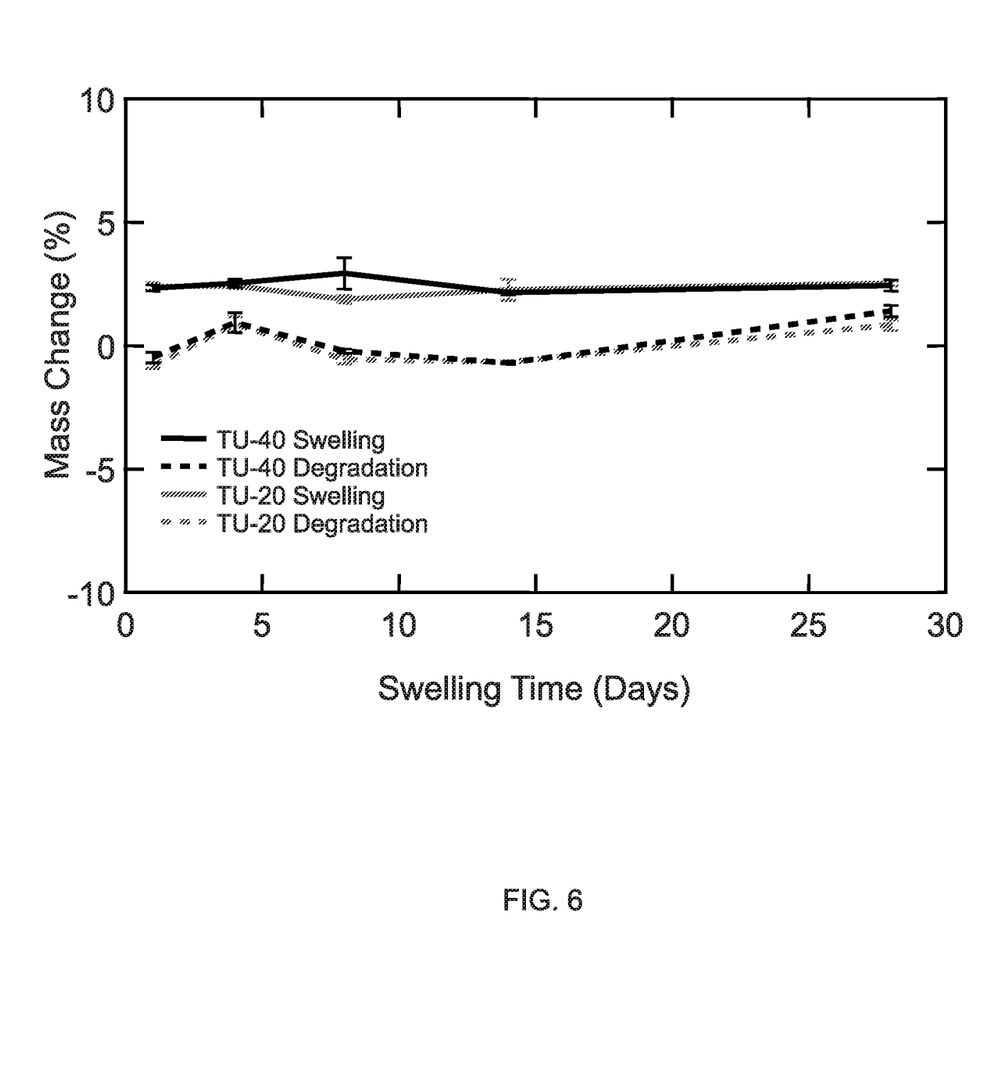
FIG. 6 presents example swelling and degradation responses of sample embodiments of the amorphous thermoset thiourethane polymers as disclosed herein.

FIG. 6 presents example swelling and degradation responses of sample embodiments of the amorphous thermoset thiourethane polymers as disclosed herein.

As illustrated in FIG. 6, the substrates show substantially identical behavior, gaining approximately 2% of their mass in water and showing no significant mass loss after four weeks.

Cytotoxicity Testing:

Cytotoxicity assays based on material extracts were carried out in accordance with International Organization for Standards (ISO) protocol "10993-5: Biological evaluation of medical devices". Here, substrate formulations were tested against positive and negative controls (Tygon-F-4040-Lubricant Tubing and complete cell medium, respectively) in order to determine normalized cell viability percentage. Extract treatments that resulted in viability percentages less than 70% were considered evidence of material cytotoxicity.

NCTC clone 929 fibroblasts (ATCC, USA) were seeded in a polystyrene 24 well plate at a density of 8,000 cells/well and incubated for 48 hours at 5% CO2, 95% relative humidity, and 37° C. in complete cell medium (EMEM supplemented with 10% horse serum) to allow for adhesion and proliferation. Material extracts were produced by separately incubating sterilized samples of SMP (5.5 cm×4.5 mm×24 µm) and positive control materials (OD: 0.794 cm, ID: 0.476 cm, 0.6 cm in length) in individual wells containing 1.65 mL of complete cell medium at 37° C. for 24 hours. Following incubation, cell medium was either exchanged for material extract medium (50/100%) or fresh medium in the case of negative controls. Cells were then incubated for an additional 24 hours prior to live/dead assays.

Live/dead cell staining was carried out using a LIVE/DEAD Cytotoxicity Kit for mammalian cells (Thermo Fisher, L3324). Briefly, cells were washed 3× in PBS and incubated in complete cell medium containing 2 µM Calcein AM (CaAM) and 4 µM Ethidium Homodimer (EthD-1) at 37° C. for 10 min CaAM and EthD-1 dyes selectively stain the cytoplasm of live cells and the nucleus of apoptotic cells, respectively. Epifluorescence images (n=4 fields of view per well) were collected on an inverted microscope (Nikon Ti eclipse) using a 10× objective. Live/dead cell counts were carried out using ImageJ (NIH) software. Cell viability percentage was defined as the ratio of CaAM-labeled cells to the total number of cells. The reported percentages were normalized to those calculated for negative control wells. Reported error bars represent standard deviations.

Figure 7:
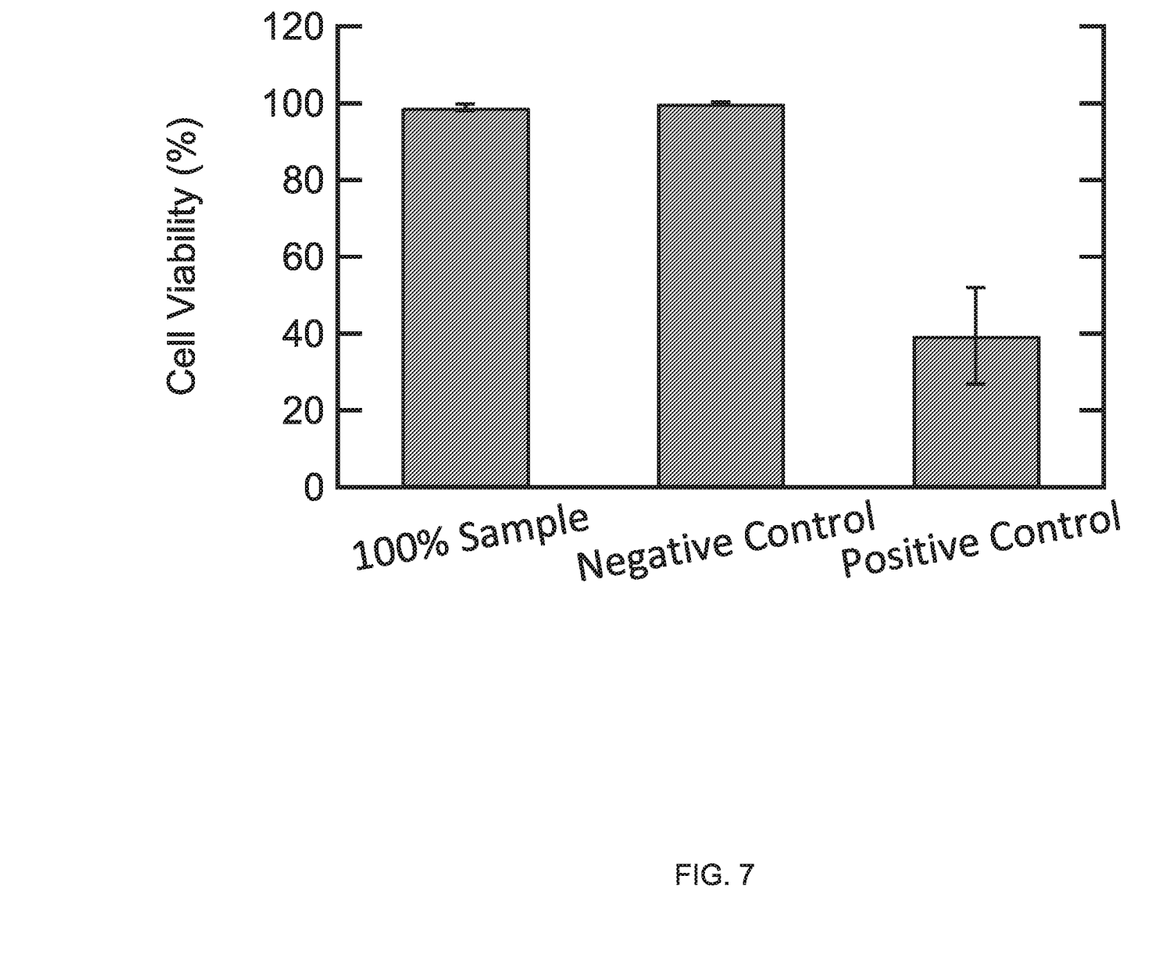
FIG. 7 presents average and standard deviations of the cell viability in the presence of sample embodiments of the amorphous thermoset thiourethane polymers as disclosed herein.

FIG. 7 presents average and standard deviations of the cell viability in the presence of sample embodiments of the amorphous thermoset thiourethane polymers as disclosed herein.

The sample extract provided statistically equal cell viability to the negative control, while the positive (cytotoxic) control had only 40% cell viability compared to the negative. The toxicity testing results suggests that there were no remaining unreacted isocyanates, or other toxic chemicals, present in sufficient concentrations in the samples to cause substantial cell death and that the substrate itself has little to no effect on cell viability.

Device Manufacturability Testing:

Bio-electronic devices were fabricated by curing the pre-polymer solutions corresponding to TU-20 and TU-40 between glass slides separated by 30 µm foil spacers. One slide was coated with a 400 nm layer of gold prior to curing, the other was cleaned by successive washings with acetone and isopropanol. The samples were cured for 30 minutes under 365 nm irradiation in a UVP CL-1000L ultraviolet crosslinker and post-cured at 100° C. for at least two hours. Following post-cure, the slides were separated leaving the polymer substrate adhered to the clean glass slide with the 400 nm layer of gold adhered to the polymer substrate surface. The gold was patterned using photolithographic techniques. A 5 µm layer of the pre-polymer resin was spin-coated onto the surface of the device prior to being cured and post-cured using the same procedure as above. This layer was then etched and titanium nitride electrodes were deposited on the surface using photolithographic techniques. The devices were then cut from the substrate using a Newport Spectra-Physics 355 nm Q-switched DPSS (Diode Pumped Solid State) Nd:YAG (Neodymium Yttrium Aluminium Garnet) nanosecond laser with a 8 µm spot size before being separated from the underlying glass.

Figure 8:
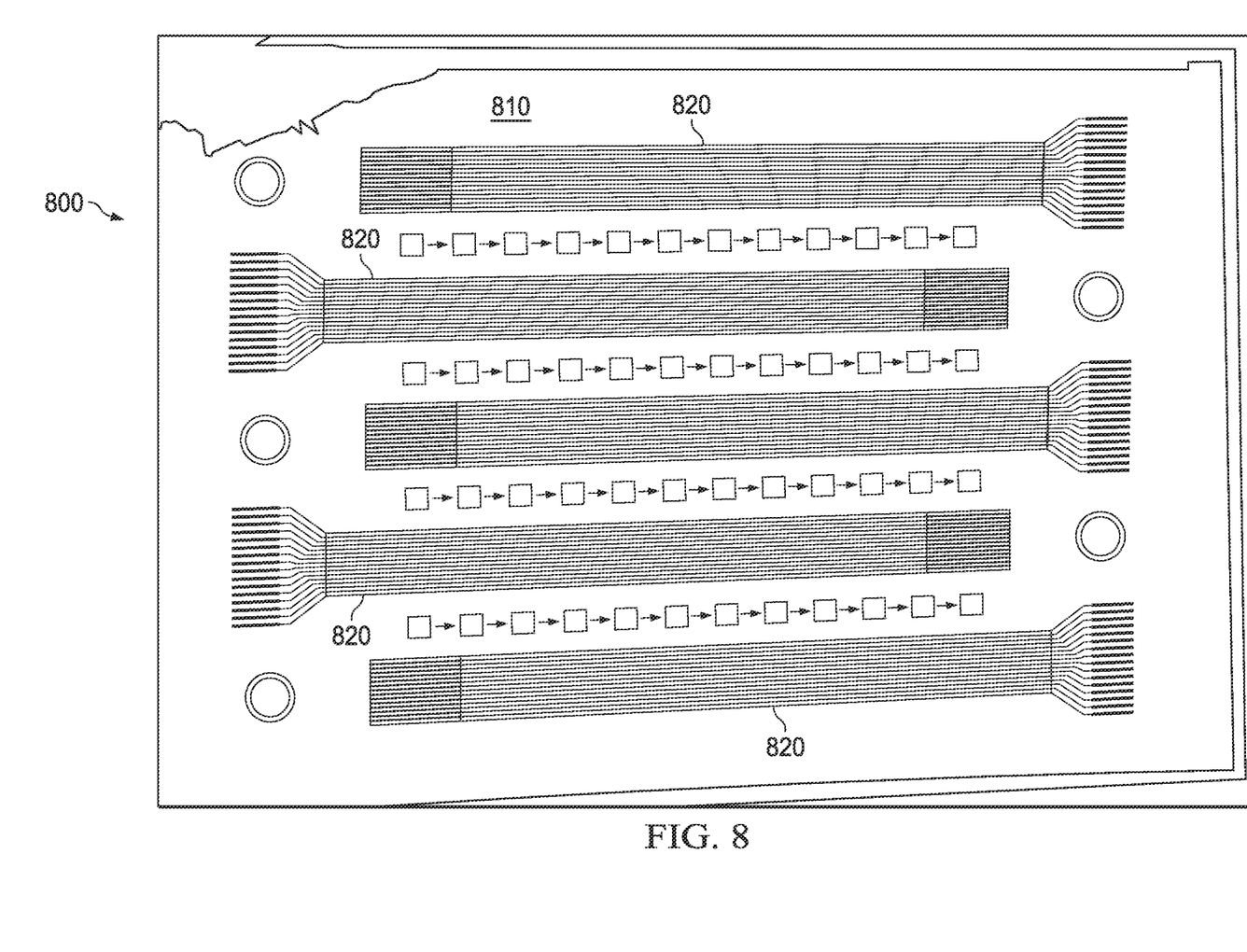
FIG. 8 presents a line drawing of bio-electronic devices formed on a substrate composed of an embodiment of the amorphous thermoset thiourethane polymers disclosed herein.

FIG. 8 presents a line drawing of bio-electronic devices 800 formed on a substrate 810 composed of an embodiment of the amorphous thermoset thiourethane polymers disclosed herein. The figure shows that devices, having substrates composed of such polymers with patterned metal lines 820 thereon, can be manufactured with the above-disclosed device fabrication process.

The substrates made from embodiments of the disclosed amorphous thermoset thiourethane polymers have glassy moduli of almost 2 GPa at physiological temperatures, but decrease to approximately 6 MPa following water uptake. The increased glassy modulus of the substrate is thought to be sufficient to prevent excessive buckling prior to complete insertion, but the higher degree of softening will more closely match living tissue (e.g. neural tissue). This is thought to be primarily due to the slightly higher degree of swelling present in the amorphous thermoset thiourethane polymers samples, e.g., as compared to thiol-ene polymers. The increased polarity of the thiourethane bond and lower crosslink density of the substrate are thought to allow more water uptake, at about 2% or higher, which is higher than some thiol-ene/acrylate polymer embodiments having swelling ratios of about 1.5%. This difference in swelling is thought to result in the amorphous thermoset thiourethane polymers samples having an over 25° C. shift in glass transition which is higher than about 20° C. shifts for some embodiments of thiol-ene/acrylate polymers. We believe that the water uptake will facilitate such amorphous thermoset thiourethane polymers samples to undergo a complete transition from glassy to rubbery when implanted in living tissue.

The polymer samples tested appear to have long-term viability and no observable cytotoxic effects. Embodiments of these samples had no observable degradation within 28 days of exposure to simulated physiological conditions. The dry tensile performance of the tested sample also suggests that substrates composed of these polymers will be resistant to mechanical failure at common failure points such as the connector of some types of bio-electronic devices. The wet tensile behavior of the tested samples shows substantial 3-order-of magnitude softening under simulated in vivo conditions while remaining tough. We believe that these features will help delay implanted device failure.

We believe that there is a general need for tougher substrates to limit device failure. For example, the longevity of softening spinal cord stimulator and/or recording devices and implantable cortical probes if these devices are constructed on tough substrates, e.g., such as devices tethered to the skull or spinal cord can experience substantial motion. This also expected to be the case for other bio-electronic devices implanted in different locations such as around nerves, in nerves or as plexus blankets For example, if softening devices bridge neighboring vertebra in the epidural space on the spinal column they can experience high shear forces. An important design paradigm is to make substrates as thin as possible so as to be less invasive. A tough polymer, such embodiments of the amorphous thermoset thiourethane polymers disclosed herein, that still soften under in vivo conditions can facilitate forming thin but durable implantable neural electronic devices.

For example, if softening devices are tethered to the skull in head caps, e.g., bridging the space between the base of the skull and the dura/pia mater, the devices can be exposed to large tethering forces and deformations due to motion of the skull and neck relative to motion of the brain. Bio-electronic devices using polymer substrates that are not able to cope with such deformations can result in premature mechanical device failure. We believe that tougher materials that still undergo softening, such as embodiments of the amorphous thermoset thiourethane polymers disclosed herein, may serve to act as robust substrates to resist failure while maintaining the benefits of having a modulus that more closely match that of living tissue.

What is claimed is:

1. An amorphous thermoset thiourethane polymer, comprising:
    a sequential chain of a first type of monomer covalently bonded to a second type of monomer via thiourethane linkages, wherein the first type of monomer includes two or more thiol functional groups and the second type of monomer includes two or more isocyanate functional groups, and softening of the polymer occurs around a glass transition temperature of the polymer and the polymer has a melt temperature that is higher than the glass transition temperature which does not disrupt the softening.

2. The polymer of claim 1, wherein the polymer has a glass transition Tg in a range from about 0° C. to 80° C.

3. An amorphous thermoset thiourethane polymer, comprising:
    a sequential chain of a first type of monomer covalently bonded to a second type of monomer via thiourethane linkages, wherein the first type of monomer includes two or more thiol functional groups and the second type of monomer includes two or more isocyanate functional groups, wherein the polymer has a rubbery modulus in a range from about 0.01 MPa to 100 MPa.

4. The polymer of claim 1, wherein the first type of monomer includes one or more of:
    Trimethylolpropane tris(3-mercaptopropionate); Trimethylolpropane tris(2-mercaptoacetate); Pentaerythritol tetrakis(2-mercaptoacetate); Pentaerythritol tetrakis(3-mercaptopropionate); 2,2'-(Ethylenedioxy)diethanethiol; 1,3-Propanedithiol; 1,2-Ethanedithiol; 1,4-butanedithiol; 1,5-pentanedithiol; 1,6-hexanedithiol; 1,9-nonanedithiol; xylene dithiol; Thiobis(benzenethiol); 1,4-Butanediol bis(thioglycolate); 1,4-bis(3-mercaptobutylyloxy)butane; Tris [2-(3-mercaptopropionyloxy)ethyl] isocyanurate; 3,4-ethylenedioxythiophene; 1,10-Decanedithiol; Tricyclo [5.2.1.02,6] decanedithiol; Benzene-1,2-dithiol; and Trithiocyanuric acid.

5. The polymer of claim 1, wherein the second type of monomer includes one or more of:
    hexamethylene diisocyanate; isophorone diisocyanate; diisocyanatobutane; diisocyanatooctane; 1,3,5-Tris(6-isocyanatohexyl)-1,3,5-triazinane-2,4,6-trione; phenylene diisocyanate; xylylene diisocyanate; tolyene diisocyanate; cyclohexylene diisocyanate; toluene isocyanate; and methylenebis(phenyl isocyanate).

6. The polymer of claim 1, further including a third type of monomer having a single thiol functional group or a single isocyanate functional group.

7. The polymer of claim 6, wherein the third type of monomer having the single thiol functional group includes one or more of: 1-butanethiol; 1-hexanethiol; 1-heptanethiol; 1-octanethiol; 1-nonanethiol; 1-dec anethiol; and 1-octadecanethiol.

8. The polymer of claim 6, wherein the third type of monomer having the single isocyanate functional group includes one or more of: propyl isocyanate; 1-pentyl isocyanate; hexyl isocyanate; octyl isocyanate; nonyl isocyanate; sec-butyl isocyanate; 2-ethylhexyl isocyanate; cyclopentyl isocyanate; and 1-isocyanato-3-methylbutane.

9. The polymer of claim 1, wherein the first type of monomer includes a linear main chain monomer having the thiol-functionalized groups at ends of the chain and the second type of monomer includes a linear main chain monomer having the isocyanate functional groups at ends of the chain, and, a bulky non-crystallizable segment-containing monomer or a tri- or higher functionalized isocyanate monomer.

10. The polymer of claim 9, wherein a total mole percentage the thiol functional groups of the first type of monomer equals about 100 mole percent of the linear main chain monomer having the thiol-functionalized groups, and, a total mole percentage of the isocyanate groups of the second type of monomer equals about 5 to 25 mole percent of the linear main chain monomer having the isocyanate functional groups, about 55 to 65 mole percent of the bulky non-crystallizable segment-containing monomer and about 20 to 40 mole percent the tri- or higher functionalized isocyanate monomer, wherein the total mole percentage of the isocyanate functional groups is substantially equal to the total mole percentage of the thiol functional groups of the first type of monomer.

11. The polymer of claim 9, wherein the linear main chain monomer having the thiol-functionalized groups is 2,2'-(Ethylenedioxy)diethanethiol, the linear main chain monomer having the isocyanate functional groups is hexamethylene diisocyanate, the bulky non-crystallizable segment-containing monomer is isophorone diisocyanate, and the tri- or higher functionalized isocyanate monomer is Tris(6-isocyanatohexyl)isocyanurate.

12. A method of synthesizing an amorphous thermoset thiourethane polymer, comprising:
    forming a mixture that includes a first type of monomer and a second type of monomer, wherein the first type of monomer and the second type of monomer are mutually miscible liquids; and
    adding to the mixture a non-nucleophillic base catalyst having a pKa greater than 7 to thereby initiate an anionic step-growth polymerization reaction to form a sequential chain of the first type of monomer covalently bonded to the second type of monomer via thiourethane linkages, wherein the first type of monomer includes two or more thiol functional groups and the second type of monomer includes two or more isocyanate functional groups, and the polymer has a rubbery modulus in a range from about 0.01 MPa to 100 MPa.

13. The method of claim 12, wherein the mixture is solvent free.

14. The method of claim 12, wherein the adding of the non-nucleophillic base catalyst to the mixture includes:
    adding a photolatent base to the mixture, and
    irradiating the mixture with UV or visible light to decompose the photolatent base into the non-nucleophillic base, wherein the non-nucleophillic base includes a tertiary amine.

15. The method of claim 12, wherein the adding of the non-nucleophillic base catalyst to the mixture includes:
adding a tertiary amine containing catalyst that is soluble in the mixture, and
heating the mixture to a temperature of about 100° C. for at least about 1 hour.

16. The method of claim 12, wherein a total mole percentage of the isocyanate groups in the mixture is substantially equal to a total mole percentage of the thiol functional groups of the first type of monomer in the mixture.

17. A bio-electronic device, comprising:
a substrate composed of an amorphous thermoset thiourethane polymer, the amorphous thermoset thiourethane polymer including:
a sequential chain of a first type of monomer covalently bonded to a second type of monomer via thiourethane linkages, wherein the first type of monomer includes two or more thiol functional groups and the second type of monomer includes two or more isocyanate functional groups, and the polymer has a rubbery modulus in a range from about 0.01 MPa to 100 MPa.

18. The bio-electronic device of claim 17, further including patterned gold lines adhered to the amorphous thermoset thiourethane polymer.

19. A method of manufacturing a bio-electronic device, comprising:
providing first and second glass substrates, the substrates spaced apart by a gap, wherein a major surface of the first glass substrates facing the gap is coated with a layer of gold;
forming an amorphous thermoset thiourethane polymer on the gold layer, including:
placing a mixture in the gap such that the mixture contacts of the layer of gold, the mixture including a first type of monomer and a second type of monomer, wherein the first type of monomer and the second type of monomer are mutually miscible liquids; and
adding to the mixture a non-nucleophillic base catalyst having a pKa greater than 7 to thereby initiate an anionic step-growth polymerization reaction to form a sequential chain of the first type of monomer covalently bonded to the second type of monomer via thiourethane linkages, wherein the first type of monomer includes two or more thiol functional groups and the second type of monomer includes two or more isocyanate functional groups, and the polymer has a rubbery modulus in a range from about 0.01 MPa to 100 MPa.

20. The method of claim 19, further including:
separating the glass substrates from each other, wherein one side of the amorphous thermoset thiourethane polymer adheres to a major surface of the second glass substrate and the gold layer is adhered to an opposite side of the amorphous thermoset thiourethane polymer;
photolithographically patterning the gold layer to form lines of the bio-electronic device; and
separating the amorphous thermoset thiourethane polymer from the major surface of the second glass substrate.

21. The polymer of claim 3, wherein the polymer has a glass transition Tg in a range from about 0° C. to 80° C.

22. The polymer of claim 3, wherein the first type of monomer includes one or more of:
Trimethylolpropane tris(3-mercaptopropionate); Trimethylolpropane tris(2-mercaptoacetate); Pentaerythritol tetrakis(2-mercaptoacetate); Pentaerythritol tetrakis (3-mercaptopropionate); 2,2'-(Ethylenedioxy)diethanethiol; 1,3-Propanedithiol; 1,2-Ethanedithiol; 1,4-butanedithiol; 1,5-pentanedithiol; 1,6-hexanedithiol; 1,9-nonanedithiol; xylene dithiol; Thiobis(benzenethiol); 1,4-Butanediol bis(thioglycolate); 1,4-bis(3-mercaptobutylyloxy)butane; Tris [2-(3-mercaptopropionyloxy)ethyl] isocyanurate; 3,4-ethylenedioxythiophene; 1,10-Decanedithiol; Tricyclo [5.2.1.02,6] decanedithiol; Benzene-1,2-dithiol; and Trithiocyanuric acid.

23. The polymer of claim 3, wherein the second type of monomer includes one or more of:
hexamethylene diisocyanate; isophorone diisocyanate; diisocyanatobutane; diisocyanatooctane; 1,3,5-Tris(6-isocyanatohexyl)-1,3,5-triazinane-2,4,6-trione; phenylene diisocyanate; xylylene diisocyanate; tolyene diisocyanate; cyclohexylene diisocyanate; toluene isocyanate; and methylenebis(phenyl isocyanate).

24. The polymer of claim 3, further including a third type of monomer having a single thiol functional group or a single isocyanate functional group.

25. The polymer of claim 24, wherein the third type of monomer having the single thiol functional group includes one or more of: 1-butanethiol; 1-hexanethiol; 1-heptanethiol; 1-octanethiol; 1-nonanethiol; 1-decanethiol; and 1-octadecanethiol.

26. The polymer of claim 24, wherein the third type of monomer having the single isocyanate functional group includes one or more of: propyl isocyanate; 1-pentyl isocyanate; hexyl isocyanate; octyl isocyanate; nonyl isocyanate; sec-butyl isocyanate; 2-ethylhexyl isocyanate; cyclopentyl isocyanate; and 1-isocyanato-3-methylbutane.

27. The polymer of claim 3, wherein the first type of monomer includes a linear main chain monomer having the thiol-functionalized groups at ends of the chain and the second type of monomer includes a linear main chain monomer having the isocyanate functional groups at ends of the chain, and, a bulky non-crystallizable segment-containing monomer or a tri- or higher functionalized isocyanate monomer.

28. The polymer of claim 27, wherein a total mole percentage the thiol functional groups of the first type of monomer equals about 100 mole percent of the linear main chain monomer having the thiol-functionalized groups, and, a total mole percentage of the isocyanate groups of the second type of monomer equals about 5 to 25 mole percent of the linear main chain monomer having the isocyanate functional groups, about 55 to 65 mole percent of the bulky non-crystallizable segment-containing monomer and about 20 to 40 mole percent the tri- or higher functionalized isocyanate monomer, wherein the total mole percentage of the isocyanate functional groups is substantially equal to the total mole percentage of the thiol functional groups of the first type of monomer.

29. The polymer of claim 27, wherein the linear main chain monomer having the thiol-functionalized groups is 2,2'-(Ethylenedioxy)diethanethiol, the linear main chain monomer having the isocyanate functional groups is hexamethylene diisocyanate, the bulky non-crystallizable segment-containing monomer is isophorone diisocyanate, and the tri- or higher functionalized isocyanate monomer is Tris(6-isocyanatohexyl)isocyanurate.

30. An amorphous thermoset thiourethane polymer, comprising:
a sequential chain of a first type of monomer covalently bonded to a second type of monomer via thiourethane linkages, wherein the first type of monomer includes two or more thiol functional groups and the second type of monomer includes two or more isocyanate functional groups, wherein:

the first type of monomer includes a linear main chain monomer having the thiol-functionalized groups at ends of the chain and the second type of monomer includes a linear main chain monomer having the isocyanate functional groups at ends of the chain, and, a bulky non-crystallizable segment-containing monomer or a tri- or higher functionalized isocyanate monomer, and a total mole percentage the thiol functional groups of the first type of monomer equals about 100 mole percent of the linear main chain monomer having the thiol-functionalized groups, and, a total mole percentage of the isocyanate groups of the second type of monomer equals about 5 to 25 mole percent of the linear main chain monomer having the isocyanate functional groups, about 55 to 65 mole percent of the bulky non-crystallizable segment-containing monomer and about 20 to 40 mole percent the tri- or higher functionalized isocyanate monomer, wherein the total mole percentage of the isocyanate functional groups is substantially equal to the total mole percentage of the thiol functional groups of the first type of monomer.

31. The polymer of claim 30, wherein the linear main chain monomer having the thiol-functionalized groups is 2,2'-(Ethylenedioxy)diethanethiol, the linear main chain monomer having the isocyanate functional groups is hexamethylene diisocyanate, the bulky non-crystallizable segment-containing monomer is isophorone diisocyanate, and the tri- or higher functionalized isocyanate monomer is Tris(6-isocyanatohexyl)isocyanurate.

* * * * *